US007199116B2

(12) United States Patent
Zenk

(10) Patent No.: US 7,199,116 B2
(45) Date of Patent: Apr. 3, 2007

(54) METHOD OF MODULATING THE BASAL METABOLIC RATE OF A DIETING MAMMAL BY ADMINISTRATION OF A METABOLIC MODULATING AGENT TO THE DIETING MAMMAL

(75) Inventor: John Zenk, Minnetrista, MN (US)

(73) Assignee: Humanetics Corporation, Eden Prairie, MN (US)

( * ) Notice: Subject to any disclaimer, the term of this patent is extended or adjusted under 35 U.S.C. 154(b) by 622 days.

(21) Appl. No.: 10/340,980

(22) Filed: Jan. 13, 2003

(65) Prior Publication Data

US 2004/0138303 A1 Jul. 15, 2004

(51) Int. Cl.
*A61K 31/56* (2006.01)
(52) U.S. Cl. .................. 514/178; 514/177; 514/182
(58) Field of Classification Search .............. 514/178, 514/177, 182
See application file for complete search history.

(56) References Cited

U.S. PATENT DOCUMENTS

| | | | |
|---|---|---|---|
| 4,666,898 A | | 5/1987 | Coleman et al. |
| 4,920,115 A | | 4/1990 | Nestler et al. |
| 5,296,481 A | * | 3/1994 | Partridge et al. ........... 514/178 |
| 5,424,463 A | | 6/1995 | Lardy et al. |
| 5,506,223 A | | 4/1996 | Lardy et al. |
| 5,807,848 A | | 9/1998 | Lardy |
| 6,399,085 B1 | | 6/2002 | Zenk et al. |
| 6,465,446 B1 | | 10/2002 | Dykstra |

FOREIGN PATENT DOCUMENTS

| | | |
|---|---|---|
| DE | 873699 | 4/1953 |
| JP | 45-37770 | 3/1966 |
| WO | WO 02/43737 | 6/2002 |

OTHER PUBLICATIONS

Wester's II New Riverside University Dictionary, 1984, p. 376.*
Yen, Terence, et al. (1977) "Prevention of Obesity in $A^{vy}/a$ Mice by Dehydroepiandrosterone", *Lipids*, vol. 12, No. 5, (409-413).
Schwartz, Arthur G. et al. (1981) "Dehydroepiandrosterone: An Anti-Obesity and Anti-Carcinogenic Agent", *Nutrition and Cancer An International Journal*; vol. 3, No. 1 (46-53).
Cleary, Margot P. et al. (1983) "Effect of Dehydroepiandrosterone on Body Weight and Food Intake in Rats", *Nutrition and Behavior*; vol. 1, No. 2 (127-136).
Staber, Lisa D. et al. (1983) "Effects of Dietary Dehydroepiandrosterone on Body Weight and Food Consumption in Lethal Yellow ($A^y/A^w$) and White-Bellied Agouti ($A^w/A^w$) Mice (Strain 129/Sv)", *Proceedings of the South Dakota Academy of Science*; vol. 62 (154-162).
Weindruch, Richard et al. (1984) "Food Intake Reduction and Immunologic Alterations in Mice Fed Dehydroepiandrosterone", *Experimental Gerontology*, vol. 19 (297-304).

Shepherd, Alene et al. (1984) "Metabolic Alterations after Dehydroepiandrosterone Treatment in Zucker Rats", *American Journal of Physiology*, vol. 246, No. 2 (123-128).
Coleman, Douglas L. (1985) "Antiobesity Effects of Etiocholanolones in Diabetes (db), Viable Yellow ($A^{vy}$), and Normal Mice", *Endocrinology*, vol. 117, No. 6 (2279-2283).
Cleary, Margot P. et al. (1986) "Anti-Obesity Effect of Two Different Levels of Dehydroepiandrosterone in Lean and Obese Middle-Aged Female Zucker Rats", *International Journal of Obesity* 10, 193-204.
Tagliaferro, Anthony R. (1986) Effects of Dehyroepiandrosterone Acetate on Metabolism, Body Weight and Composition of Male and Female Rats [1,2], *The Journal of Nutrition*, vol. 116, No. 10 (1977-1983).
Nestler, John E. et al. (1988) Dehydroepiandrosterone Reduces Serum Low Density Lipoprotein Levels and Body Fat but Does not Alter Insulin Sensitivity in Normal Men, *The Journal of Clinical Endocrinology & Metabolism*, vol. 66, No. 1 (57-61).
Mohan, Pamarthi F. (1988) "Effect of Short-term DHEA Administration on Liver Metabolism of Lean and Obese Rats", *American Journal of Physiology*, vol. 255, No. 1 (1-8).
Lardy, Henry et al. (1989) "Dehydroepiandrosterone Induces Enzymes That Permit Thermogenesis and Decrease Metabolic Efficiency", *Hormones, Thermogenesis, and Obesity*, Institute for Enzyme Research, University of Wisconsin-Madison, Madison, Wisconsin, USA. (415-426).
Nestler, John E. et al. (1989) Dehydroepiandrosterone: Effects on Insulin Sensitivity, Serum Lipid Levels, and Body Composition in Normal Men, *Hormones, Thermogenesis, and Obesity*, Division of Endocrinology and Metabolism, Medical College of Virginia/Virginia Commonwealth University; Richmond, Virginia, USA (405-414).
Schauer, Jane E. (1989) "Effects of Acute and Chronic Exercise in Rats on Energy Transduction under the Influence of Dehydroepiandrosterone and β-Agonist", *Hormones, Thermogenesis, and Obesity*, Institute for Enzyme Research, Madison, Wisconsin, USA., Uniformed Services University of Health Sciences, F. Edward Herbert School of Medicine, Bethesda, Maryland, USA. (485-501).
Cleary, M. P. (1989) Antiobesity Effect of Dehydroepiandrosterone in the Zucker Rat, *Hormones, Thermogenesis, and Obesity*, The Hormel Institute, University of Minnesota, Austin, Minnesota, USA (365-376).
MacEwen, E. Gregory (1989) "Antiobesity and Hypocholesterolemic Activity of Dehydroepiandrosterone (DHEA) in the Dog", *Hormones, Thermogenesis, and Obesity*, Department of Medical Sciences, School of Veterinary Medicine, University of Wisconsin-Madison, Madison, Wisconsin, USA (399-404).
Su, Ching-Yuan (1988) Induction of Hepatic Mitochondrial Glycerophosphate Dehydrogenase and Malic Enzyme 1. Effects of Dehydroepiandrosterone 2. Effects of Dehydroepiandrosterone-Related Steroids and Cytochrome P-450 Inducers, University of Wisconsin-Madison (1-126).

(Continued)

*Primary Examiner*—Sreenivasan Padmanabhan
*Assistant Examiner*—Jennifer Kim
(74) *Attorney, Agent, or Firm*—Sherrill Law Offices, PLLC

(57) ABSTRACT

Modulating the metabolism of a dieting mammal by administering to the dieting mammal the metabolic modulating agent 7-oxo DHEA or a pro-drug thereof incapable of in vivo conversion to testosterone.

9 Claims, No Drawings

OTHER PUBLICATIONS

Lardy, Henry et al., (1990), "Biochemical Aspects of Obesity", Annual Revue.

Usiskin, Keith S. et al. (1990) "Lack of Effect of Dehydroepiandrosterone in Obese Men", *International Journal of Obesity*, vol. 14, No. 5 (457-463).

Mortola, J. F. et al. (1990) "The Effects of Oral Dehydroepiandrosterone on Endocrine-Metabolic Parameters in Postmenopausal Women", *Clinical Endocrinology & Metabolism*, vol. 71, No. 3 (696-704).

Mohan, Pamarthi F. et al. (1990) Effects of Dehydroepiandrosterone Treatment in Rats with Diet-Induced Obesity[1,2], *The Journal of Nutrition*, vol. 120, No. 9 (1103-1114).

Welle, Stephen et al. (1990) "Failure of Dehydroepiandrosterone to Influence Energy and Protein Metabolism in Humans", The Journal of Clinical Endocrinology & Metabolism, vol. 71, No. 5 (1259-1264).

Nestler, John E. et al. (1991) "Metabolism and Actions of Dehydroepiandrosterone in Humans", *The Journal of Steroid Biochemistry and Molecular Biology* vol. 40, No. 4-6 (599-605).

Su, Ching-Yuan et al. (1991) Induction of Hepatic Mitochondrial Glycerophosphate Dehydrogenase in Rats by Dehydroepiandrosterone[1], *J. Biochem.*, 110 (207-213).

Bobyleva, Valentina et al. (1993) "Concerning the Mechanism of Increased Thermogenesis in Rats Treated with Dehydroepiandrosterone", *Journal of Bioenergetics and Biomembranes*, vol. 25, No. 3 (313-321).

Morales, Arlene J. et al. (1994) Effects of Replacement Dose of Dehydroepiandrosterone in Men and Women of Advancing Age, *Journal of Clinical Endocrinology and Metabolism*, vol. 78, No. 6 (1360-1367).

Regelson, William et al. (1994) "Dehydroepiandrosterone (DHEA)—the Multifunctional Steroid", *The Aging Clock The Pineal Gland and Other Pacemakers in the Progression of Aging and Carcinogenesis*, vol. 719 (564-575).

Lardy, Henry et al. (1995) "Ergosteroids: Induction of Thermogenic Enzymes in Liver of Rats Treated with Steroids Derived from Dehydroepiandrosterone", *Proc. Natl. Acad. Sci. USA*, vol. 92 (6617-6619).

[Author unknown] (1995) "Guidelines for the Approval and Use of Drugs to Treat Obesity", *Obesity Research*, vol. 3, No. 5 (473-478).

Shealy, C. Norman (1995) "A Review of Dehydroepiandrosterone (DHEA)", *Integrative Physiological and Behavioral Science*, vol. 30, No. 4 (308-313).

Casson, Peter R. et al. (1995) "DHEA Administration to Humans: Panacea or Palaver?", *Seminars in Reproductive Endocrinology*, vol. 13, No. 4 (247-256).

Kurzman, Ilene D., (1998), The Effect of Dehydroepiandrosterone combined with a Low-Fat Diet in Spontaneously Obese Dogs: A Clinical Trial, Obesity Research, vol. 6 No. 1.

AdvantRx Corporation (2000), "Eating and Exercise Plan".

Active Nutraceuticals (2002), ". . . experience the miracle".

Humanetics Corporation (2002), "7 Keto The #1 Selling Non-Stimulant Weight Loss Ingredient".

Zenk, John L. M.D. (1999), "Humanetics Health Facts", *7 Keto*.

Humanetics Corporation (2001), www.humaneticscorp.com/.

Humanetics Corporation, "Push Down and Turn-Up The Safety and Potency of DHEA".

Humanetics Corporation (1998), "Squeeze Sides and Lift-Up the Benefits of DHEA Without the Worry".

The Effects of the Ergosteroid 7-Oxo-dehydroepiandrosterone on Mitochondrial Membrane Potential: Possible Relationship to Thermogenesis, Bobyleva et al., Archive of Biochemistry and Biophysics, vol. 342, No. 1, May 1. pp. 122-128, 1997, Article No. BB979955.

The Effect of 7-Keto Naturalean™ on Weight Loss: A Randomized, Double-Blind, Placebo-Controlled Trial, Current Therapeutic Research, Zenk et al., vol. 63, No. 4, Apr. 2002, pp. 263-272.

A Randomized, Double-Blind, Placebo-Controlled Study of 3-Acetyl-7-Oxo-Dehydroepiandrosterone in Healthy Overweight Adults, Current Therapeutic Research, Kalman et al., vol. 61, No. 7, Jul. 2000, pp. 435-442.

The Effect of the Ergosteroid 7-Oxo-Dehydroepiandrosterone on Mitochondiral Membrane Potential: Possible Relationship to Thermogenesis, Archives of Biochemistry and Biophysics, Bobyleva et al., vol. 341, No. 1, May 1997, pp. 122-128.

Safety and Pharmacokinetic study with escalating doses of 3-Acetyl-7-oxo-dehydroepiandrosterone in healthy male volunteers, Clin Invest Med, Davidson et al., vol. 23, n[5], Oct. 2000, pp. 300-310.

* cited by examiner

METHOD OF MODULATING THE BASAL METABOLIC RATE OF A DIETING MAMMAL BY ADMINISTRATION OF A METABOLIC MODULATING AGENT TO THE DIETING MAMMAL

FIELD OF INVENTION

The invention relates to methods of modulating the Basal Metabolic rate of a mammal.

BACKGROUND

Mammals, particularly humans, are believed to have a Basal Metabolic rate which defines the rate at which they convert calories to energy. It is widely believed that the Basal Metabolic rate is influenced by dieting, with the body reacting to a reduced caloric intake by slowing down the Basal Metabolic rate of the dieter. This diet induced reduction in the Basal Metabolic rate is one of the reasons thought to be responsible for the ineffectiveness of achieving weight loss by dieting.

Accordingly, a need exists for a method of safely modulating the Basal Metabolic rate of a dieting mammal.

SUMMARY OF THE INVENTION

The basal metabolic rate, or resting energy expenditure, of a dieting mammal may be modulated by administering a metabolic modulating agent to the dieting mammal. The metabolic modulating agent is 7-oxo DHEA or a pro-drug thereof incapable of in vivo conversion to testosterone.

DETAILED DESCRIPTION OF A PREFERRED EMBODIMENT

Definitions

As utilized herein, including the claims, the term "dieting" means eating and drinking sparingly with the intent to lose weight.

As utilized herein, including the claims, the term "7-oxo DHEA" means $\Delta$5-androstene-3-ol-7, 3-ol-7,17-dione.

As utilized herein, including the claims, the term "3-acetyl 7-oxo DHEA" means $\Delta$5-androstene-3-acetoxy-7,17-dione.

Description

It is widely believed that dieting is an ineffective means for achieving weight loss because the body reacts to the reduced caloric intake by slowing down the metabolism of the dieter. I have surprisingly discovered that 7-oxo DHEA is effective for modulating the metabolism of a dieting mammal so as to prevent or at least moderate any diet-induced decrease in metabolism. Such moderation of the metabolism should be effective for accelerating the weight loss achievable by dieting.

The Metabolic Modulating Agent

The metabolic modulating agent effective for modulating the Basal Metabolic rate of a dieting mammal is the steroid $\Delta$5-androstene-3$\beta$-ol-7,17 dione (7-oxo DHEA). 7-oxo DHEA is a derivative of dehydroepiandrosterone (DHEA). 7-oxo DHEA does not appreciably stimulate, increase or otherwise enhance the production of sex hormones. The steroid is commercially available from a number of sources including Steraloids, Inc. of Wilton, N.H. A number of procedures are available for synthesizing $\Delta$5-androstene-3$\beta$-ol-7,17 dione from DHEA, with one such procedure described in U.S. Pat. No. 5,296,481.

Pro-drugs of 7-oxo DHEA (i.e., compounds readily metabolized in vivo to the active 7-oxo DHEA) may also be usefully employed. One example of a pro-drug is the commercially available $\Delta$5-androstene-3$\beta$-acetyl-7,17 dione (3-acetyl 7-oxo DHEA). The 3$\beta$-acetyl group is hydrolyzed in vivo by esterases located in the blood and various tissue to produce the active 7-oxo DHEA, and is believed to be less susceptible to oxidation during the manufacturing process relative to 7-oxo DHEA. Other suitable pro-drugs include $\Delta$5-androstene-3$\beta$, 17$\beta$-diol-7-one, $\Delta$5-androstene-3$\beta$, 7$\alpha$-diol-17-one, $\Delta$5-androstene-3$\beta$, 7$\beta$-diol-17-one and the corresponding acetyl esters of these steroids.

Administration

Administration Route

The metabolic modulating agent can be administered by virtually any of the commonly accepted practices for the administration of pharmaceutical preparations including specifically, but not exclusively, mucosal administration, oral consumption, ocular administration, subcutaneous injection, transdermal administration, etc. Oral administration is generally preferred.

Mucosal administration of the metabolic modulating agent includes such routes as buccal, endotracheal, nasal, pharyngeal, rectal, sublingual, vaginal, etc. For administration through the buccal/sublingual/pharyngeal/endotracheal mucosal, the metabolic modulating agent may be formulated as an emulsion, gum, lozenge, spray, tablet or an inclusion complex such as cyclodextrin inclusion complexes. Nasal administration is conveniently conducted through the use of a sniffing powder or nasal spray. For rectal and vaginal administration the metabolic modulating agent may be formulated as a cream, douche, enema or suppository.

Oral consumption of the metabolic modulating agent may be effected by incorporating the metabolic modulating agent into a food or drink, or formulating the metabolic modulating agent into a chewable or swallowable tablet or capsule.

Ocular administration may be effected by incorporating the metabolic modulating agent into a solution or suspension adapted for ocular application such as drops or sprays.

Subcutaneous administration involves incorporating the metabolic modulating agent into a pharmaceutically acceptable and injectable carrier.

For transdermal administration, the metabolic modulating agent may be conveniently incorporated into a lipophilic carrier and formulated as a topical creme or adhesive patch.

Dose Rate

The range of dosages and dose rates effective for achieving the desired modulation of metabolism may be determined in accordance with standard industry practices.

I claim:

1. A method of modulating the metabolism of a dieting mammal comprising administration of a metabolic modulating agent to the dieting mammal wherein the metabolic modulating agent is 7-oxo DHEA or a pro-drug thereof incapable of in vivo conversion to testosterone.

2. The method of claim 1 wherein the metabolic modulating agent is administered orally.

3. The method of claim 2 wherein the metabolic modulating agent is administered at least once daily.

4. The method of claim 1 wherein the dieting mammal is a human.

5. The method of claim 2 wherein the dieting mammal is a human.

6. The method of claim 3 wherein the dieting mammal is a human.

7. The method of claim 4 wherein the metabolic modulating agent is 3-acetyl 7-oxo DHEA or 3-ester thereof.

8. The method of claim 5 wherein the metabolic modulating agent is 3-acetyl 7-oxo DHEA or 3-ester thereof.

9. The method of claim 6 wherein the metabolic modulating agent is 3-acetyl 7-oxo DHEA or 3-ester thereof.

* * * * *